United States Patent
Ebisawa

(10) Patent No.: US 8,358,337 B2
(45) Date of Patent: Jan. 22, 2013

(54) PUPIL DETECTION DEVICE AND PUPIL DETECTION METHOD

(75) Inventor: Yoshinobu Ebisawa, Hamamatsu (JP)

(73) Assignee: National University Corporation Shizuoka University (JP)

( * ) Notice: Subject to any disclaimer, the term of this patent is extended or adjusted under 35 U.S.C. 154(b) by 645 days.

(21) Appl. No.: 12/064,481

(22) PCT Filed: Aug. 22, 2006

(86) PCT No.: PCT/JP2006/316382
§ 371 (c)(1),
(2), (4) Date: Mar. 31, 2009

(87) PCT Pub. No.: WO2007/023798
PCT Pub. Date: Mar. 1, 2007

(65) Prior Publication Data
US 2009/0219386 A1 Sep. 3, 2009

(30) Foreign Application Priority Data
Aug. 23, 2005 (JP) ................ P2005-241728

(51) Int. Cl.
| H04N 7/18 | (2006.01) |
| H04N 5/30 | (2006.01) |
| G03B 13/00 | (2006.01) |
| G01B 9/04 | (2006.01) |
| G01J 1/20 | (2006.01) |

(52) U.S. Cl. ....... 348/78; 348/162; 348/345; 250/201.8; 250/201.9

(58) Field of Classification Search .......... 348/78, 348/162, 345; 250/201.8, 201.9
See application file for complete search history.

(56) References Cited

U.S. PATENT DOCUMENTS
| 5,621,457 A | * | 4/1997 | Ishiwaka et al. ........ 348/78 |
| 6,082,858 A | * | 7/2000 | Grace et al. ........ 351/200 |

(Continued)

FOREIGN PATENT DOCUMENTS
| JP | 2-138673 | 5/1990 |
| JP | 7-134800 | 5/1995 |

(Continued)

OTHER PUBLICATIONS
English translation of International Preliminary Report on Patentability issued on May 22, 2008 in counterpart PCT application.

(Continued)

*Primary Examiner* — Ranodhi Serrao
(74) *Attorney, Agent, or Firm* — Ostrolenk Faber LLP

(57) ABSTRACT

A pupil detection device includes a camera, a light source disposed at the camera, an optical system, and an image processing system, which are disposed so that the examinee's face is irradiated with the light from the light source from the camera, and a face image including a pupil is formed in the camera. The light source includes a first light source, having a first wavelength that makes a bright pupil image by reflection in the examinee's pupil, and a second light source having a second wavelength that makes a dark pupil image by reflection in the examinee's pupil, but otherwise exhibiting the same illumination effect as the first light source. The camera includes a first image data acquisition system using the first illumination light source, and a second image data acquisition system using the second illumination light source.

6 Claims, 17 Drawing Sheets

U.S. PATENT DOCUMENTS

| | | | |
|---|---|---|---|
| 6,152,563 A * | 11/2000 | Hutchinson et al. | 351/209 |
| 7,280,678 B2 | 10/2007 | Haven et al. | |
| 2004/0252277 A1* | 12/2004 | Chmielewski et al. | 351/209 |
| 2005/0200806 A1* | 9/2005 | Knaan et al. | 351/169 |
| 2007/0279590 A1* | 12/2007 | Ebisawa | 351/208 |

FOREIGN PATENT DOCUMENTS

| | | |
|---|---|---|
| JP | 10-221016 | 8/1998 |
| JP | 11-56782 | 3/1999 |
| JP | 2002-513176 | 5/2002 |
| JP | 2004-261598 | 9/2004 |
| JP | 2005-198743 | 7/2005 |
| JP | 2005-266868 | 9/2005 |
| WO | 99/55220 | 11/1999 |

OTHER PUBLICATIONS

Office Action issued Jan. 26, 2010 in related Japanese Patent Application No. P2006-225720.

International Search Report issued Nov. 14, 2006.

Morimoto, C.H., et al., "Pupil Detection and Tracking Using Multiple Light Sources," *Image and Vision Computing*, 18, pp. 331-335 (2000).

* cited by examiner

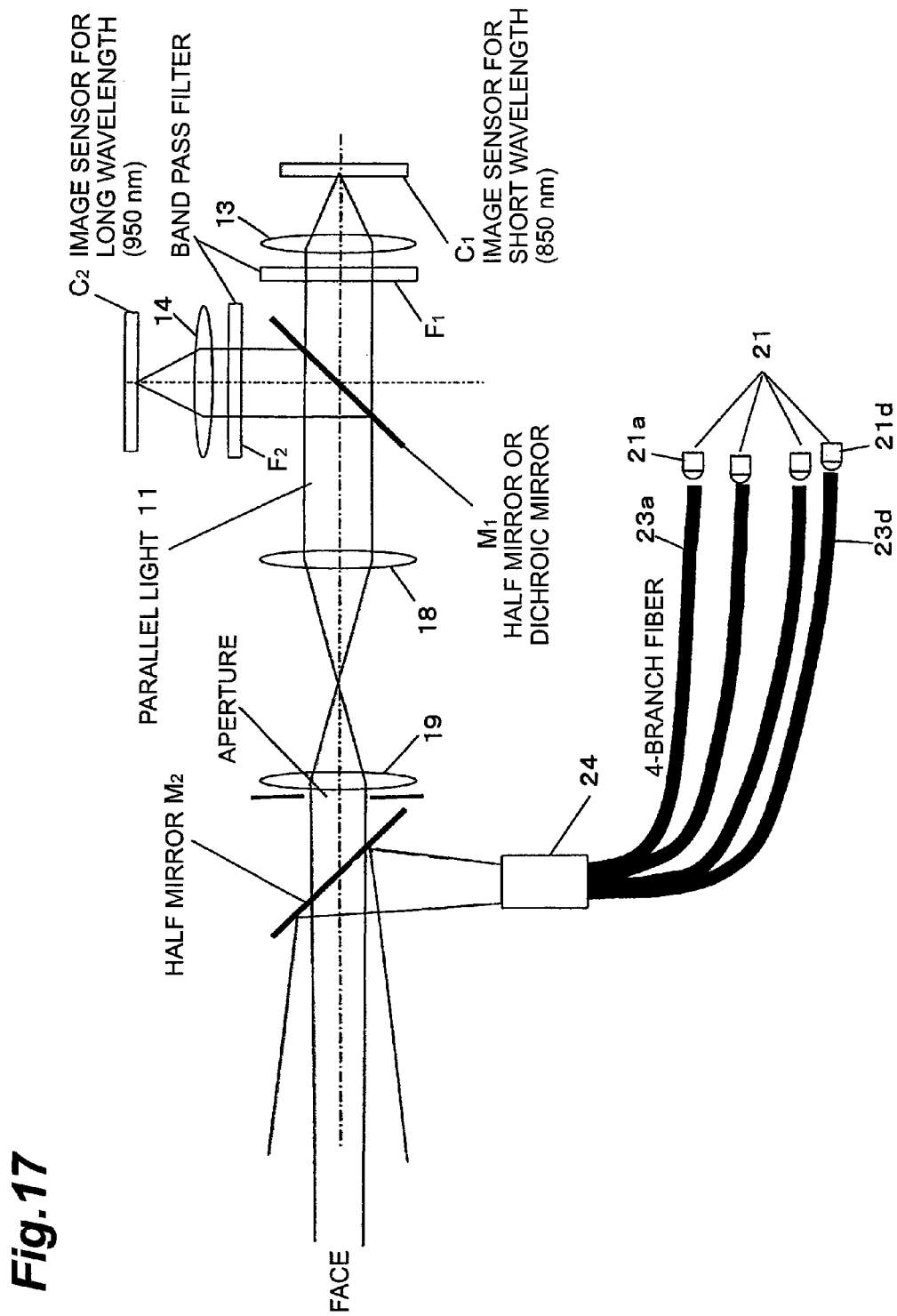

PUPIL DETECTION DEVICE AND PUPIL DETECTION METHOD

TECHNICAL FIELD

The present invention relates to a pupil detection device and a pupil detection method applicable to the field of eye gaze detection, etc., and more particularly, to a pupil detection device and a pupil detection method enabling reliable detection of a pupil even in an environment unsuitable for pupil detection due to intensive surrounding light.

BACKGROUND ART

The pupil detection has been recognized as an effective means for estimating the intention of an examinee by capturing a characteristic point of a human face, and for acquiring information about point at and from which an examinee's is looking. Many kinds of studies and inventions have been conducted in regard to the pupil detection itself and the application thereof (Patent documents 1-4 and Non-patent document 1). The pupil is excellent as a detection object because the pupil itself is small, and not only basically viewed as a circle or an ellipse from any directions, but hard to be concealed behind the eyelid, differently from an iris. By the use thereof, it has been proposed to make a pupil moving amount correspond to cursor movement on a personal computer screen, and also, the cursor can be moved relative to the movement of the head.

Further, using the pupil detection technique, there are requirements for detecting eyes, sleepiness and inattentive driving of a passenger car driver and a truck driver. In such cases, it has been desired to stably enable the pupil detection even under a bad environment such that human faces are exposed to direct sunlight.

Patent document 1: Japanese Patent Application No. 2004-73998
Patent document 2: Japanese Patent Application Laid-open No. 2004-261598
Patent document 3: Japanese Patent Publication No. 2002-513176
Patent document 4: Japanese Patent Application Laid-open No. Hei-11-56782
Non-patent document 1: "Pupil detection and tracking using multiple light sources", C. H. Morimoto, D. Koons, A. Amir, and M. Flickner, Image and Vision Computing 18 (2000), 331-335

DISCLOSURE OF THE INVENTION

Problems to be Solved by the Invention

Problems expected in detecting a bright pupil are studied. As one of the relations between a light source and a pupil in detecting the pupil, a red-eye phenomenon (bright pupil phenomenon) is known, and the above phenomenon is utilized in the pupil detection (Patent document 1).

FIG. 1 is an optical path diagram illustrating one example of the relationship among a camera C, a light source L and an eyeball EB in which the bright pupil is not observed. Light flux incident on the pupil from the light source L is shown by lines 1 and 2 shown in the figure. The light source L is positioned out of an aperture (effective diameter of the lens) of the camera C.

The examinee's eye has a refracting power, and assuming that the focus of the eyes coincides with the position of the light source L, the edges of the area in which the light flux incident on the pupil passes can be shown as lines 1' and 2'.

The image of the light source is formed on a retina, so as to form a spot on the retina. The light reflects diffusely in various directions on the retina, and a portion thereof passes through the pupil, and returns through a path inside 1'-1 and 2'-2 (oblique line portion). At this time, the light generated from the spot on the retina focuses on the light source position, and on the assumption that the light source L has no dimension, the above light passes through the light source position, and diffuses again. The above light returning from the eye is not incident on the camera aperture, and therefore, the pupil is imaged darkly by the camera.

FIG. 2 shows a case that the focus of the eye is located at a farther point than the light source (a far-sighted state).

In the above case, since the light incident on the pupil focuses behind the retina, an out-of-focus large spot is imaged on the retina. The light from the spot is output from the retina, and focuses at the focus position of the eye, passing through a path range (oblique line portion) between 1-1' and 2-2'. The above path may be understood if the spot on the retina is considered to be collected point light sources, and the focus position of the eye is taken into consideration. In the above case also, the light returning from the pupil is not incident on the camera.

Oppositely, as shown in FIG. 3, when the focus of the eye is positioned at a nearer point than the light source (a short-sighted state), the light passing through the retina focuses before the retina, and a spot having a dimension is generated on the retina. Among irregular reflection light from the spot, the light passing through the pupil passes through a path range shown by the oblique line portion in the figure. In this case also, the reflected light from the retina is not incident on the camera aperture, and therefore, the pupil is imaged as a dark portion by the camera.

Now, if the light source is disposed in the vicinity of the camera aperture as shown in FIG. 4, a portion of the reflected light from the retina is incident on the camera aperture, and therefore, the pupil is imaged brightly. However, as is apparent from this figure, it is not efficient when the detection of the pupil is intended by illuminating the pupil, because more than half of the reflected light from the retina is not incident on the camera aperture.

In the above description, a case that the pupil is large (in general, the maximum diameter of 8 mm) has been shown, and when the pupil is small (in general, the minimum diameter of 2 mm), the optical path becomes as shown in FIG. 5. To begin with, when the pupil is small, a light amount passing through the pupil becomes small (the luminance of the pupil are in proportion to the pupil area), and the luminance of the pupil is reduced, and as a result, the detection of the pupil becomes extremely difficult. Also, because a small pupil simply makes it difficult to be distinguished from the remains of eyeglass reflection after image processing, which leads to an incorrect detection. Moreover, actually, the light source has a dimension, and a certain distance is definitely required from the light source to the aperture. Therefore, the light amount returning to the camera aperture becomes extremely small.

In other words, when the pupil is large, the pupil is easy to be brightened even if the light source is relatively spaced apart from the camera aperture, but when the pupil is small, the pupil is hard to be brightened unless the light source is positioned as near as possible to the camera aperture, or ultimately, positioned inside the aperture. As shown in FIG. 6, a bright pupil is obtainable if the light source is placed coincidentally on the optical axis of the camera, which however impedes imaging.

According to the aforementioned Patent document 4, there has been proposed a method of installing a light source at the center of the camera aperture so as to obtain a bright pupil (bright eye) image. However, also in the above case, the light source itself has a dimension, and when only the center of the light source is bright, it is hard to brighten the pupil because a distance virtually exists between the light source and the aperture. Further, a most problematic issue when installing the light source inside the camera aperture is that the light source itself is imaged as a white spot, and the pupil detection is impeded, when the expansion rate of the camera is reduced, for example, when a camera lens is selected to have the expansion rate approximately sufficient for imaging the overall face positioned 80 cm ahead.

It is an object of the present invention to provide a pupil detection device and a pupil detection method, enabling reliable pupil detection even under an environment unsuitable for pupil detection due to intensive surrounding light around an examinee.

Means for Solving the Problems

In order to achieve the aforementioned object, a pupil detection device according to Claim 1 of the present invention includes a camera; a light source; an optical path forming means; and a calculation means, the optical path forming means being configured to irradiate an examinee's face of an examinee with light from the light source and to enable image formation of a face including an examinee's pupil in the camera, the pupil detection device calculating an image formed in the camera to detect the pupil. The above light source is disposed so as to enable irradiation with light from inside an aperture of the camera, and includes: a first illumination light source having a first wavelength light component to make a bright pupil by reflection in the examinee's pupil; and a second illumination light source having a second wavelength light component to make a dark pupil by reflection in the examinee's pupil and exhibiting the same illumination effect as that of the first illumination light source except for the pupil. The above camera includes: a first image data acquisition means for obtaining a first image data using the first illumination light source; and a second image data acquisition means for obtaining a second image data using the second illumination light source. The above calculation means is a means for calculating the first image data and the second image data, so as to detect the pupil.

A pupil detection method according to Claim 5 of the present invention is a method for detecting a pupil by irradiating an examinee's face with light from a light source, forming a face image including the examinee's pupil in a camera, and thereafter calculating the image obtained by the image formation in the camera using a calculation means. The pupil detection method includes the steps of: irradiating, from inside an aperture of the camera, a first wavelength light component to make a bright pupil by reflection in the examinee's pupil, and a second wavelength light component to make a dark pupil by reflection in the examinee's pupil, exhibiting the same illumination effect as the first wavelength light component except for the pupil, from the above light source; acquiring a first image data by the above camera, using the first wavelength light component; acquiring a second image data by the above camera, using the second wavelength light component; and detecting the pupil by calculating the first image data and the second image data by the above calculation means.

As the pupil detection device according to Claim 2 of the present invention, in the pupil detection device according to Claim 1, the light source is configured such that optical axes of the independent first illumination light source and second illumination light source are synthesized by the optical path forming means so as to maintain a common optical axis, and that the optical path is modified to have the common optical axis coincident with the optical axis of the camera means.

As the pupil detection device according to Claim 3 of the present invention, in the pupil detection device according to Claim 1, the light source is configured such that respective optical axes of an independent first light emission source and a second light emission source are disposed adjacent and parallel to each other and light collection is performed by a lens means, and that the optical path is modified by the optical path forming means so as to make the adjacent and parallel optical axes coincide with the optical axis of the camera means.

As the pupil detection device according to another aspect of the present invention, in the pupil detection device according to Claim 1, the calculation means is configured to detect the pupil by a differential calculation between the first image data and the second image data.

As the pupil detection device according to another aspect of the present invention, in the pupil detection device according to Claim 1, the camera means is configured to have the first image data acquisition means and the second image data acquisition means formed by dividing pixel groups of an identical image sensor in a single camera.

As the pupil detection device according to another aspect of the present invention, in the pupil detection device according to Claim 1, the camera means is configured to have the first image data acquisition means and the second image data acquisition means formed by separate cameras.

As the pupil detection device according to Claim 4 of the present invention, in the pupil detection devices according to Claim 1 to 3, there is provided a pair of pupil detection devices being disposed apart from the examinee by a certain distance and apart from each other by a certain distance, and each detecting the pupil to measure a three-dimensional position of the pupil.

Effects of the Invention

According to the pupil detection device as described in Claim 1 of the present invention, and the pupil detection method described in the Claim 5, reliable detection of a pupil can be attained.

According to the pupil detection device as described in Claim 2 of the present invention, a satisfactory illumination effect can be obtained because the light source is configured such that the optical axes of an independent first illumination light source and a second illumination light source are synthesized by a optical path forming means so as to maintain a common optical axis, and the optical path is modified to make the above common optical axis coincident with the optical axis of a camera means.

According to the pupil detection device as described in Claim 3 of the present invention, a satisfactory illumination effect can be obtained by use of more compact illumination light sources.

According to the pupil detection device as described in a further aspect of the present invention, the above calculation means can satisfactorily extract only a pupil image by a differential calculation between the first image data and the second image data.

According to the pupil detection device as described in a further aspect of the present invention, the camera means includes the first image data acquisition means and the second image data acquisition means by dividing pixel groups of an identical image sensor in a single camera, and thus a compact apparatus can be intended.

According to the pupil detection device as described in a further aspect of the present invention, the camera means includes the first image data acquisition means and the second image data acquisition means each configured of different cameras, and thus, reliable pupil detection can be attained.

According to the pupil detection device as described in Claim 4 of the present invention, there are provided a pair of pupil detection devices for measuring a three-dimensional position of the pupil by means of a range finder system.

BRIEF DESCRIPTION OF THE DRAWINGS

FIG. 17 is an optical path diagram illustrating another pupil detection device according to the present invention.

DESCRIPTION OF THE REFERENCE SYMBOLS

Figure 1:
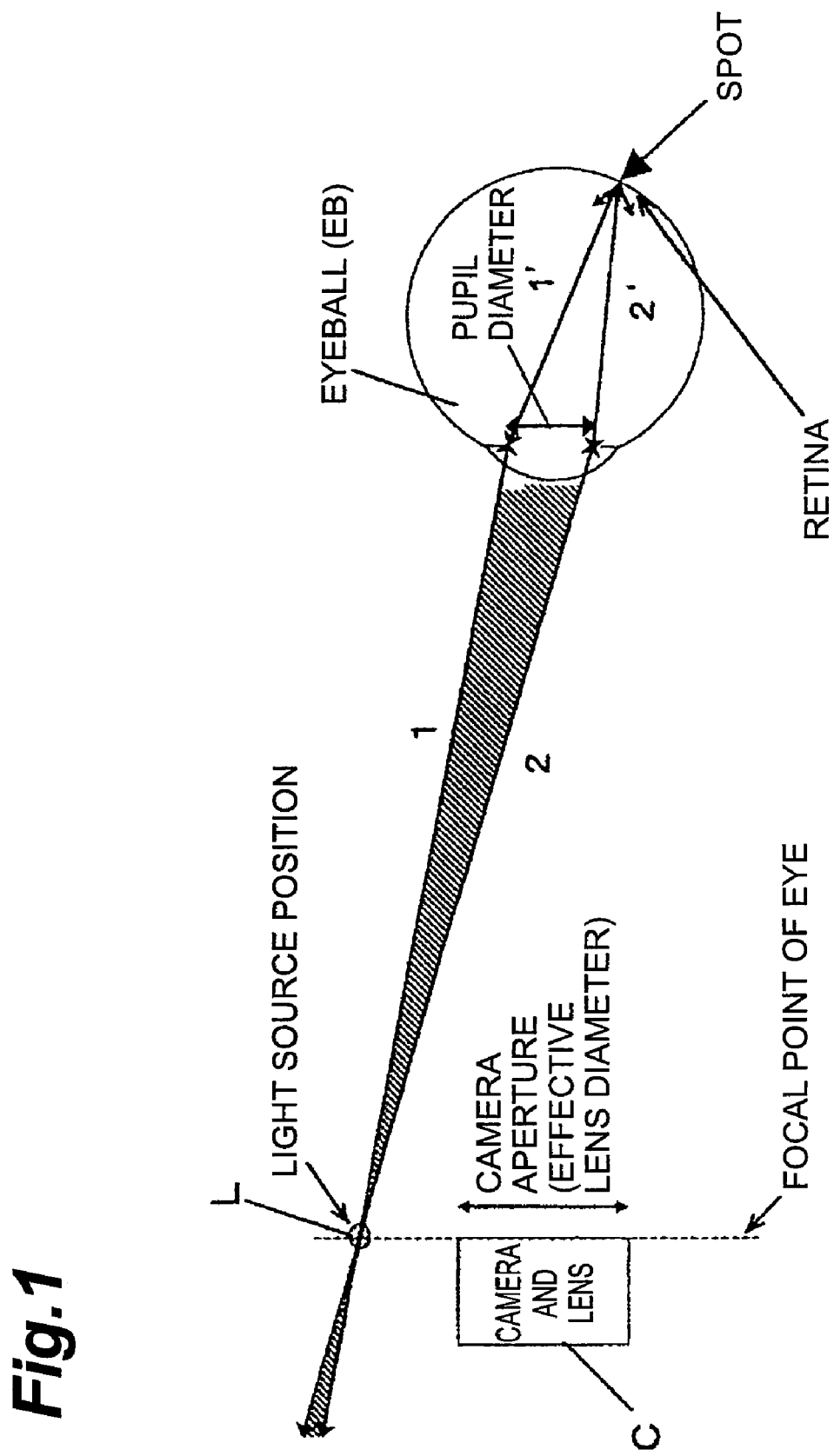
FIG. 1 is an explanatory diagram illustrating a positional relation among an eyeball, a light source and a camera to describe the reason of difficulty of detecting a bright pupil.
Figure 2:
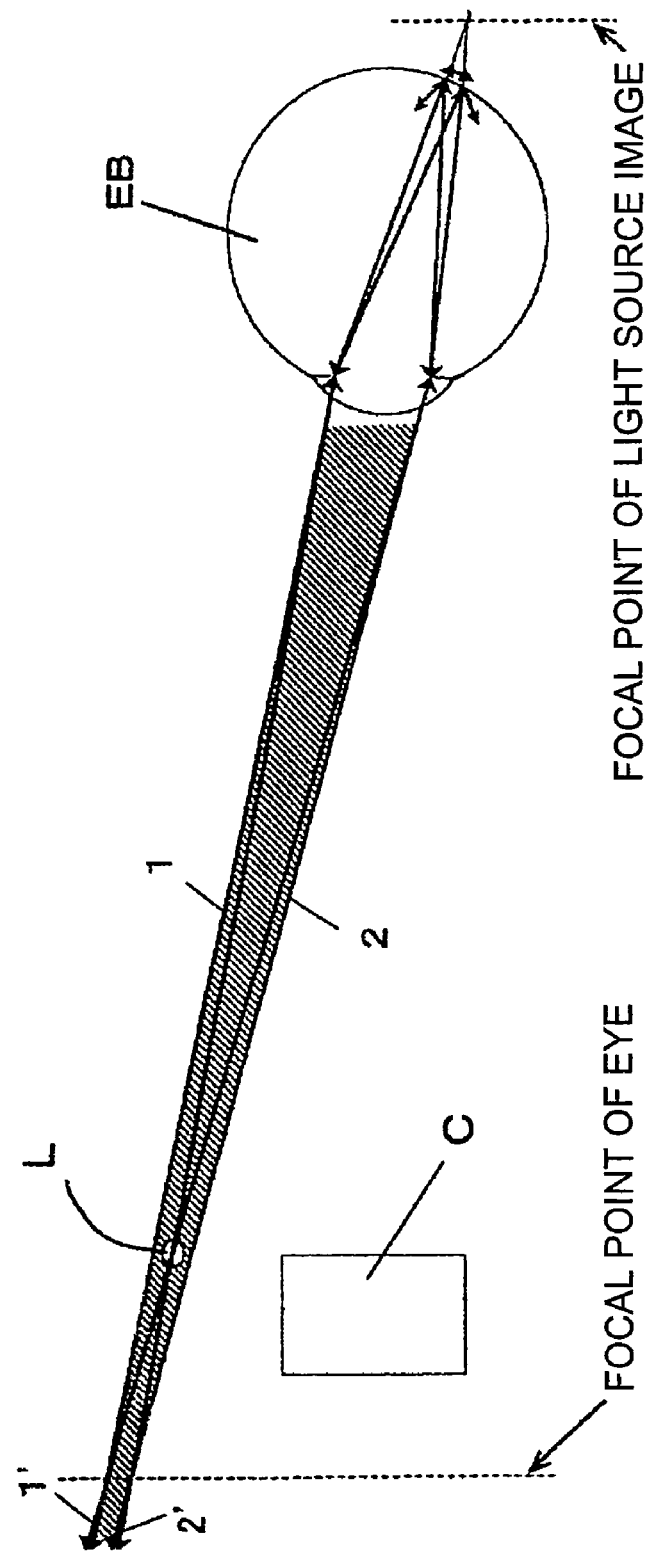
FIG. 2 is an explanatory diagram in a far-sighted state, to the identical effect of FIG. 1.
Figure 3:
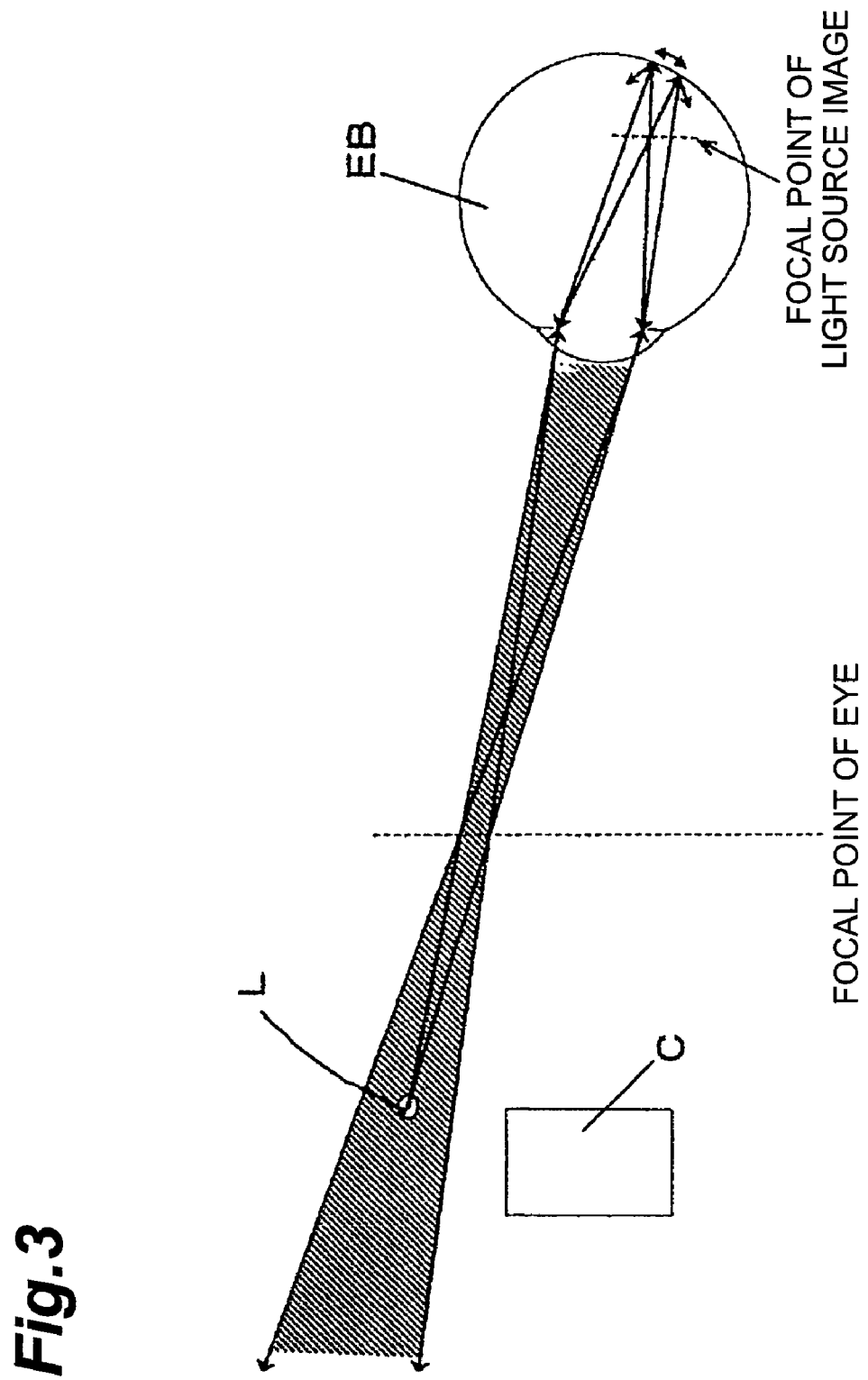
FIG. 3 is an explanatory diagram in a short-sighted state, to the identical effect of FIG. 1.
Figure 4:
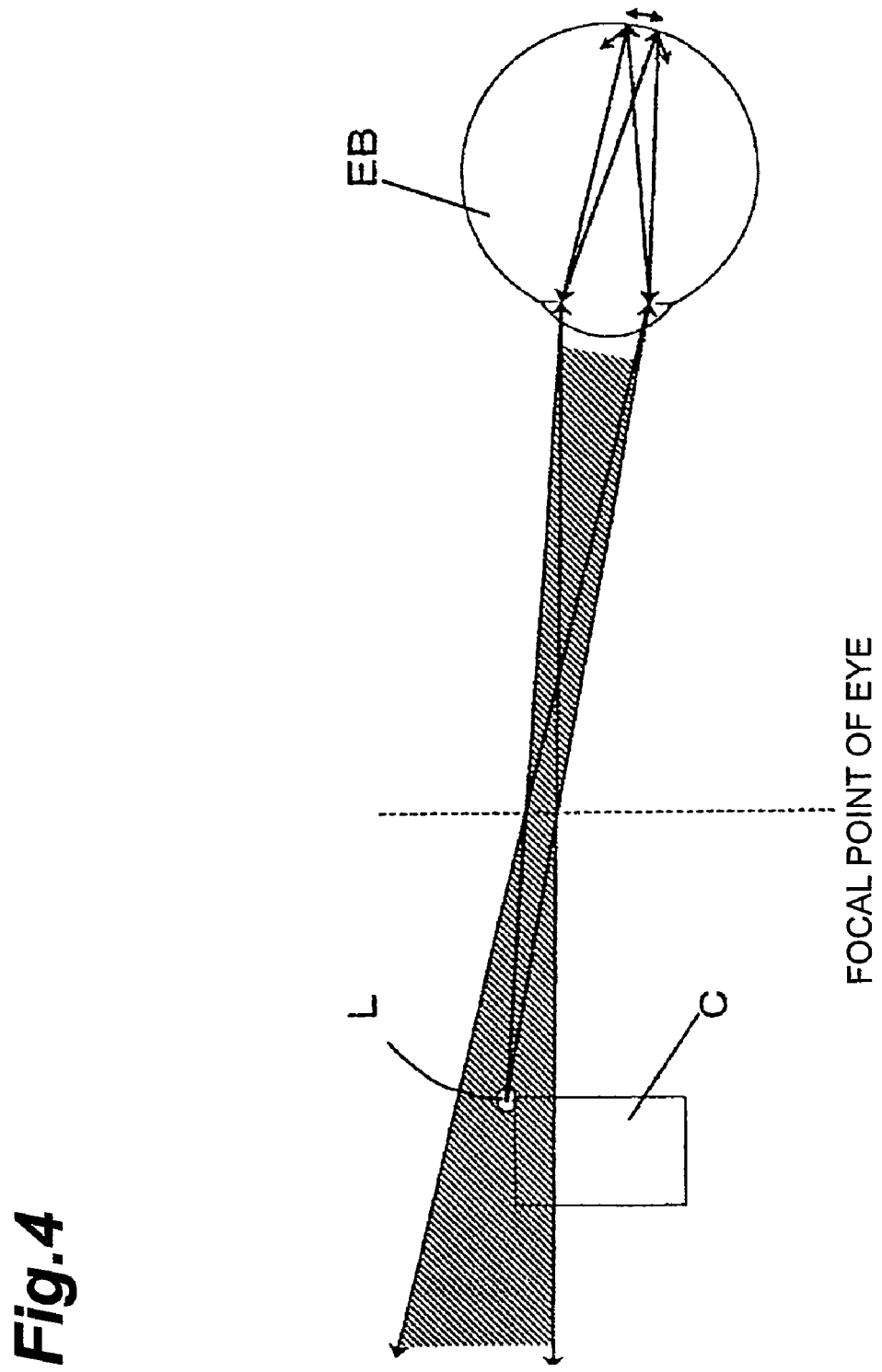
FIG. 4 is an explanatory diagram when a light source is disposed in the vicinity of a camera aperture, to the identical effect of FIG. 1.
Figure 5:
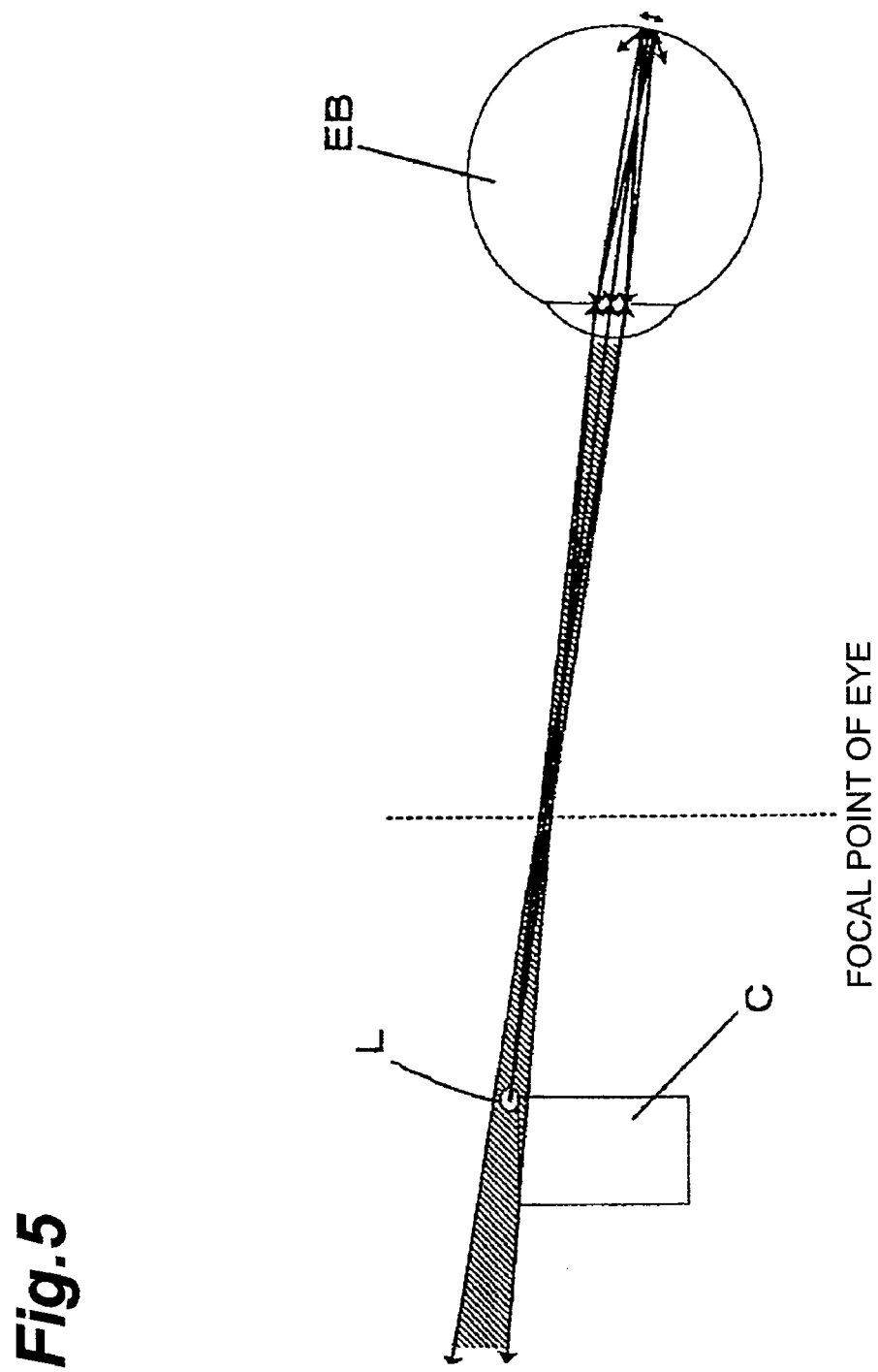
FIG. 5 is an explanatory diagram to describe a problem when a pupil is small, to the identical effect of FIG. 1.
Figure 6:
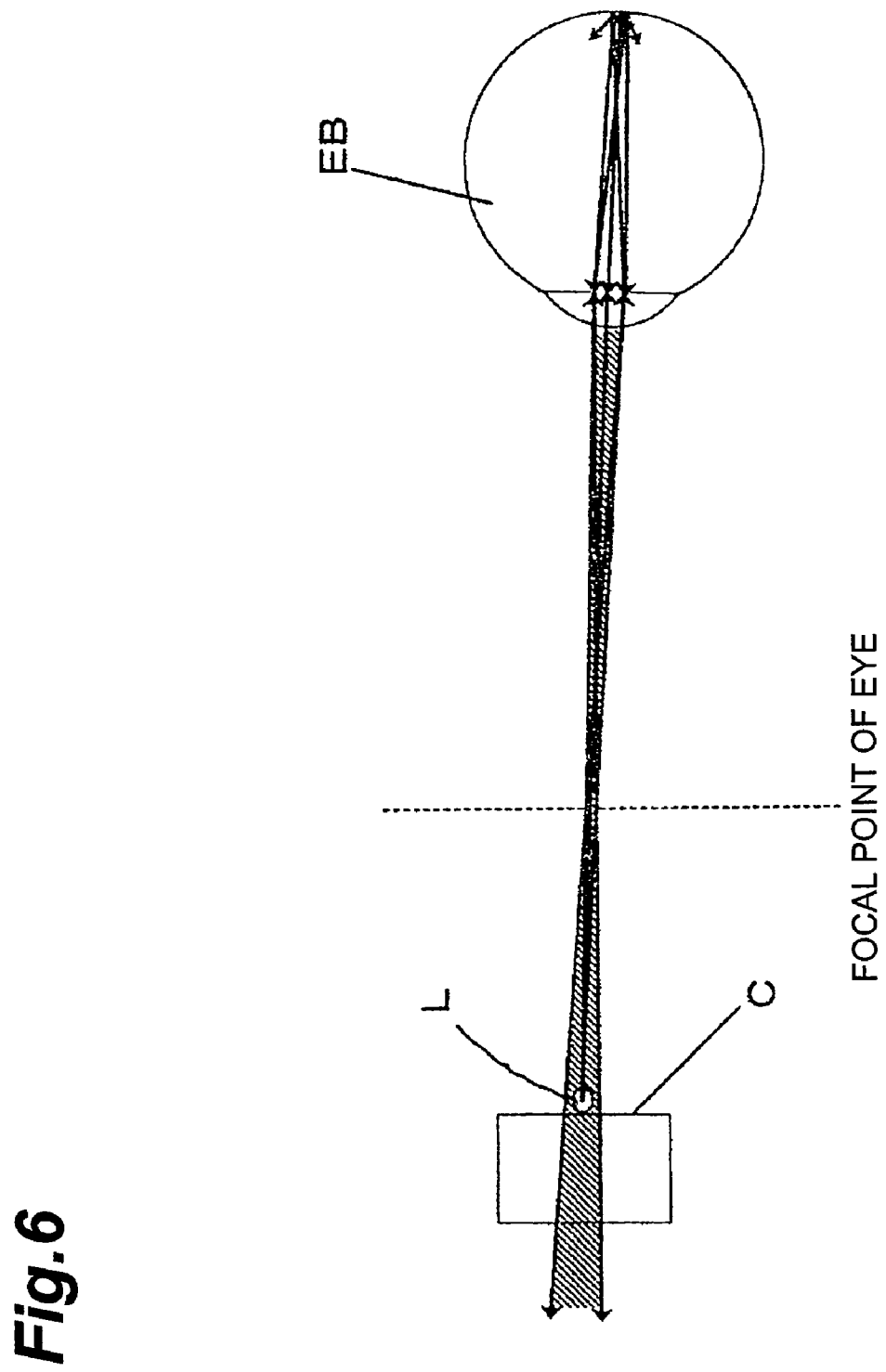
FIG. 6 is an explanatory diagram to describe a problem when a pupil is small and a light source is disposed in the camera aperture, to the identical effect of FIG. 1.

L (L1, L2, L12) 21a-21d ... light sources;
C (C1, C2) ... cameras;
EB ... eyeball;
M, $M_1$, $M_2$ ... (dichroic, half) mirrors;
F (F1, F2) ... filters.

BEST MODES FOR CARRYING OUT THE INVENTION

Hereafter, referring to the drawings, the principle of the present invention will be described first, with the comparison of the prior arts.

Figure 7:
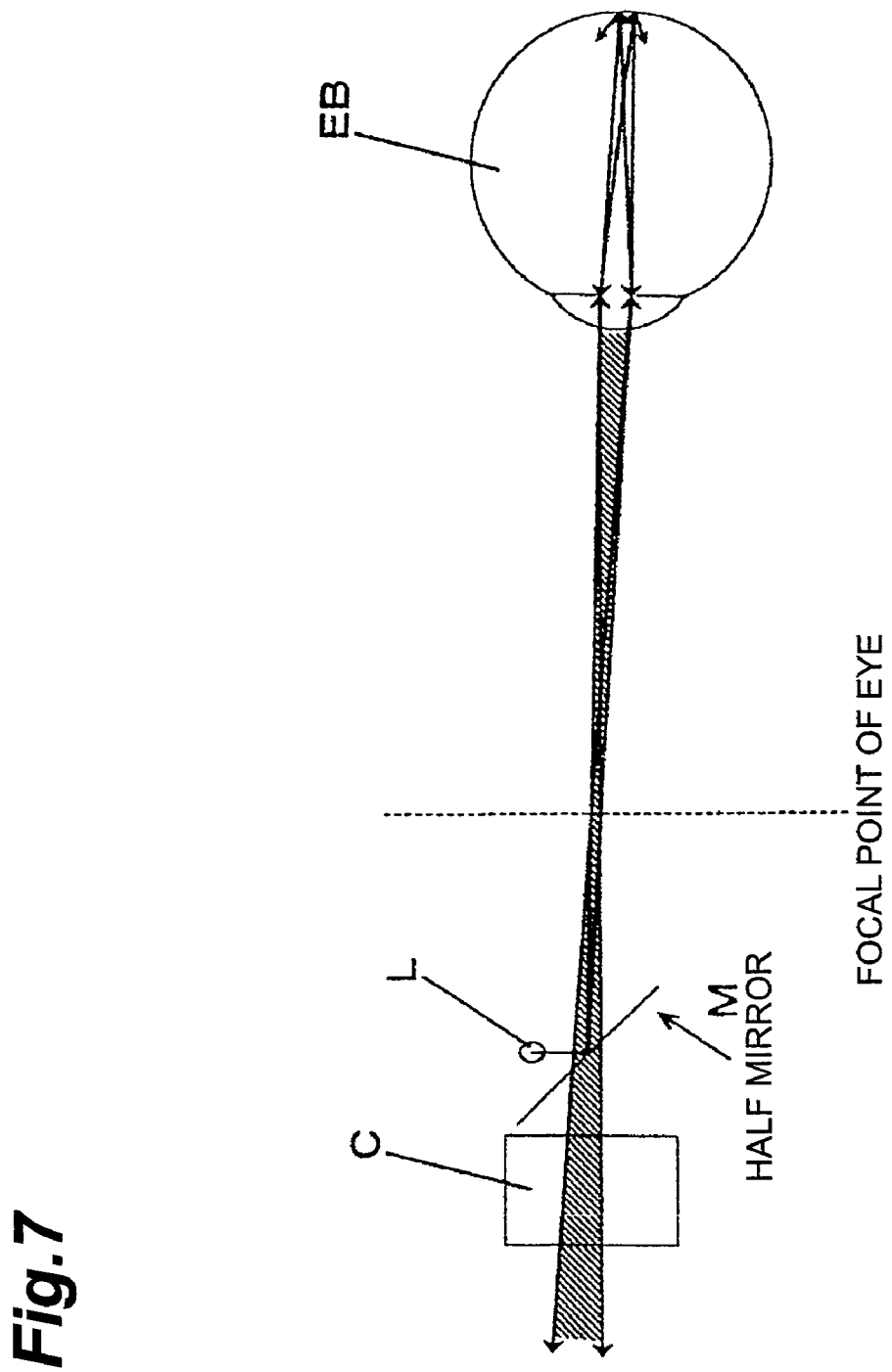
FIG. 7 is an explanatory diagram to illustrate the principle of bright pupil detection in the present invention.
Figure 8:
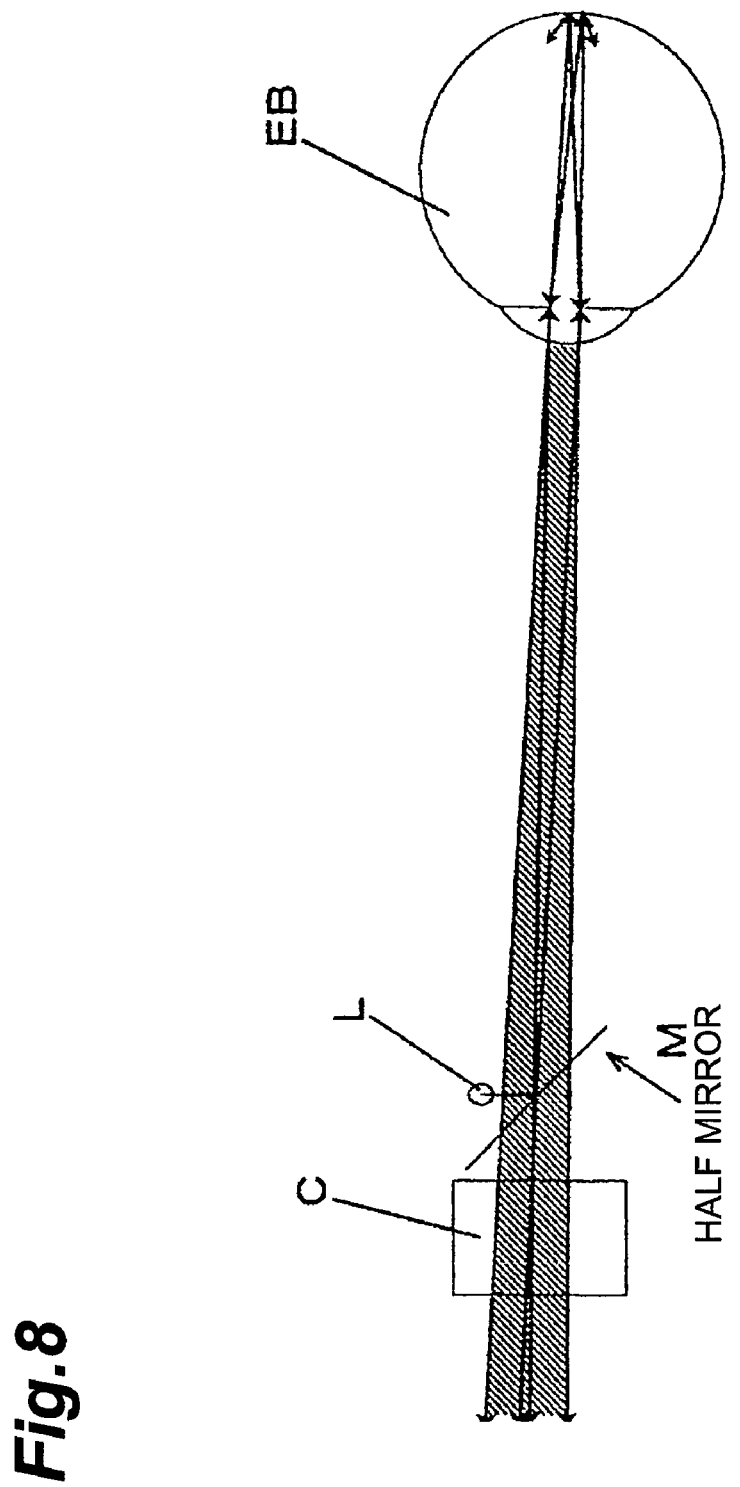
FIG. 8 is another explanatory diagram to illustrate the principle of bright pupil detection in the present invention.

FIGS. 7, 8 are explanatory diagrams for illustrating the principle of bright pupil detection, according to the present invention.

As shown in FIG. 7, an eye is irradiated with light from the light source via a half mirror M, and the light is incident on the camera aperture in such a manner that reflected light at the retina is not impeded by the light source itself. The example in this figure shows a case of a shortsighted state. In the example shown in FIG. 8, there is shown a case that an eye focus lies in an infinite far point. As in the above examples, light reflected at the retina is incident on the camera aperture whenever a pupil area is small or wherever the eye is focused.

To obtain a bright pupil image with a small pupil, desirably the light source is installed inside the camera aperture, whereas to obtain a dark pupil image it is effective to install the light source as far as possible from the camera aperture. On the other hand, if the light source for obtaining the bright pupil image is spaced apart from the light source for obtaining the dark pupil image, as described above, since light reflected by an eyeglass and light reflected on the frame of the pair of glasses are imaged in mutually different positions, it is difficult to remove them by using difference of images. Also, a luminance difference tends to occur therebetween on the face surface. Moreover, at the boundary between the face and the background, there is produced a difference such as brightness caused by one illumination and darkness due to a shadow caused by the other illumination, and as a result, the detection becomes difficult.

Therefore, according to the present invention, there are used two types of light sources generating different wavelength light components so as to cause a luminance difference only on the pupil portion, even when the light sources are placed in the same position.

A first illumination light source includes a first wavelength light component to make a bright pupil by reflection in the examinee's pupil. Also, a second illumination light source includes a second wavelength light component to make a dark pupil by reflection in the examinee's pupil, but except for the pupil, exhibits the same illumination effect as the first illumination light source.

Additionally, as described in the invention described in Patent document 3 (Japanese Patent Publication No. 2002-513176), since the reflection coefficient in the reflection on the retina are different between wavelengths of 850 nm and 950 nm, at least two types of LEDs having center wavelengths of 850 nm and 950 nm are employed. (The above center wavelengths are not limited thereto. It may be possible to have 930 nm, 970 nm, etc. instead of 950 nm, and 830 nm, 870 nm, etc. instead of 850 nm. A great change in the reflection coefficient of the retina across the boundary of approximately 900 nm is utilized. Here, the LED having a center wavelength of less than 850 nm is undesirable depending on a use, because the light emission source itself is seen bright.)

Therefore, the above bright pupil or the above dark pupil does not necessarily signify brightness or darkness greater than other portions than the pupil depending on the surrounding brightness, but signifies that the bright pupil is relatively brighter than the dark pupil.

The above-mentioned two types of LED light emission sources are installed to be equivalently in an identical position, with the light sources being placed inside the aperture to the possible extent. By the formation in such a manner, the eyeglass reflection imaged in the camera image is seen equivalently, irrespective of the lit light emission source of either wavelength. Further, the light emission source having a shorter wavelength than 900 nm (short-wavelength light source) images the pupil brighter than the light emission source having a longer wavelength than 900 nm (long-wavelength light source). The sensitivity of a camera is different depending on the wavelength, needless to say, and therefore, ideally, a luminance balance in the portions other than the pupil is to be kept in advance, by adjusting a current amount flowing in each light emission source. By such a means, only the pupil becomes highlighted in the differential image, and the detection becomes easier. Similarly, in regard to the reflected lights on the front face, the rear face, and the frame of the eyeglass, the images are canceled and deleted because the light source positions are regarded to be identical.

Now, the points of difference from the method described in the aforementioned Patent document 3 will be described in brief. In the aforementioned method, because light sources are disposed outside a camera aperture, it is difficult to detect a small pupil. According to the present invention, basically, the light sources are disposed inside the camera aperture (which does not mean that the disposition out of the camera aperture is inhibited). Accordingly, it is possible to make even a small pupil a bright pupil, and thus, the pupil can be detected. Also, in the aforementioned method, the light sources having different wavelengths are disposed in physically separate positions, and therefore, it is hard to remove the eyeglass reflection of the light sources only by obtaining a difference. According to the present invention, as will be described later, the different light sources are installed at an identical position, and accordingly, by obtaining the difference, the eyeglass reflection can be removed automatically, and the pupil can be detected easily.

The method described in the aforementioned Patent document 2 (Japanese Patent Application Laid-open No. 2004-261598) also relates to the detection of a bright pupil and a dark pupil. In the aforementioned method, one of light sources producing an identical wavelength or different wavelengths is installed in the vicinity of the optical axis of camera, and the other is installed far from the optical axis.

Two images are formed by time division when the wavelengths are identical, or by wavelength separation when the wavelengths are different, and the pupil is detected from the difference image therebetween, and however, in this case also, it is hard to remove the eyeglass reflection, because in the two images to obtain a difference, the positions of the eyeglass reflection are different.

In contrast, the light sources of two wavelengths are basically installed together inside the aperture, and the light sources of two wavelengths are installed equivalently in an identical position so as to mutually cancel the eyeglass reflection light in the two images to obtain a difference.

According to the above method, it may be possible to apply wavelength separation when the center of the pupil is required to detect accurately in case of a rapid movement of the pupil, and apply time division in other cases.

Figure 9:
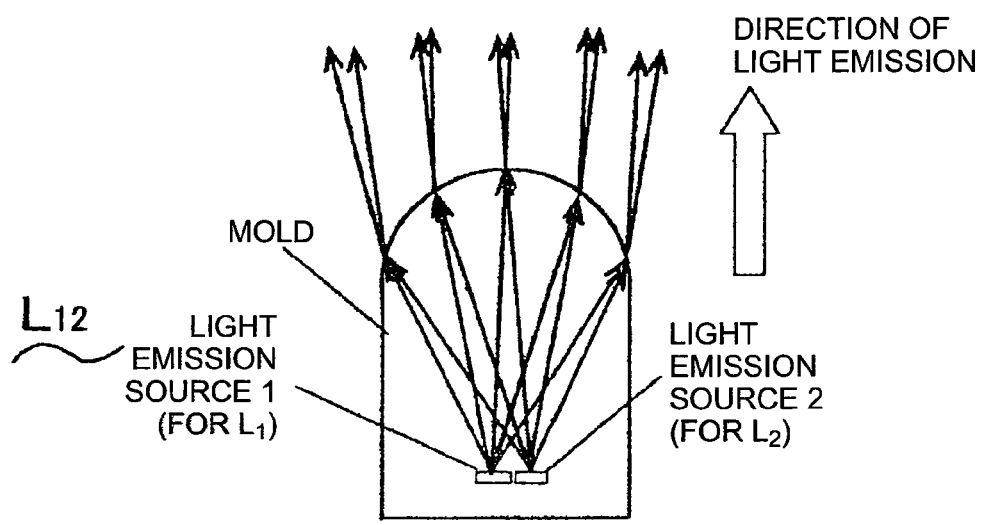
FIG. 9 is a diagram illustrating typical examples of a first and a second illumination light sources for use in a pupil detection device according to the present invention.

(Typical example of the light sources) As shown in FIG. 9, there are used two types of light emission sources (LEDs) for L1 and L2 1, 2 installed in such a manner that the respective optical axes thereof are positioned adjacent and parallel to each other, and packaged into one bullet-shaped mold (condenser lens) so that the directivity of the two types of light is substantially identical. With this arrangement, the light source (mold) viewed from the light emission direction produces an equivalent luminance distribution at an object, whichever light emission source is lit.

Accordingly, light reflected on other portions of the examinee illuminated by the above light sources, for example reflection by the eyeglass of the examinee or the like, is a reflected light exceedingly similar. Therefore, using the image difference, the eyeglass reflection etc. in the image photographed by the camera can be removed quite efficiently.

Figure 16:
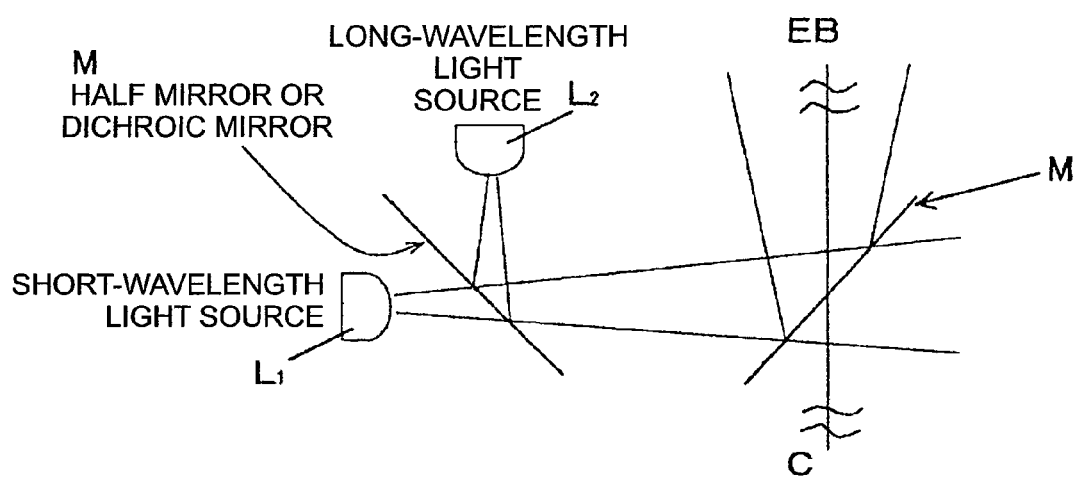
FIG. 16 is a diagram showing another typical example of a first and a second illumination light sources for use in a pupil detection device according to the present invention.

A light source having a characteristic similar to that of the light source shown in FIG. 9 is also obtainable using another optical system. For example, i) The similar optical characteristic is obtainable also by using concave-surface reflection.
ii) Also, it is possible to use a Y-branch optical fiber. LED light of short-wavelength out of the two types is made incident on one branch of the branching fiber, and LED light of long-wavelength is made incident on the other. With this arrangement, it is possible to mix light of two wavelength types, and irradiate a face with the light, using a condenser lens, so as to fit the angle of the camera object (image angle).
iii) Further, as shown in FIG. 16, by applying a dichroic mirror M to two light sources L1, L2, and for example, by reflecting most light from the long-wavelength light source and transmitting most light from the short-wavelength light source, it is possible to efficiently irradiate the eye with the both types of light. In some cases, a half mirror M may also be applicable.

Figure 13:
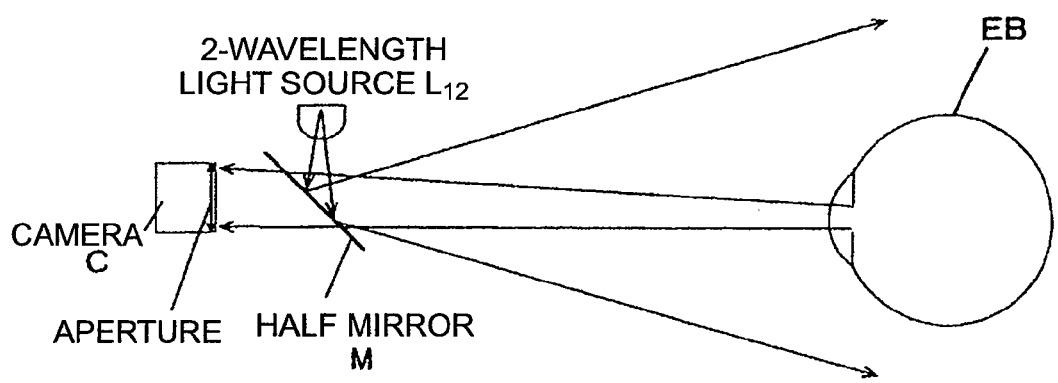
FIG. 13 is an optical path diagram illustrating another pupil detection device according to the present invention.

In the above case, taking into consideration a wavelength-to-sensitivity curve of an image sensor of the camera C, the light source power, etc, a suitable reflection-to-transmission ratio of the half mirror M may be selected so that the balance between the both can be obtained. The light thus synthesized is introduced by the half mirror M or the like so as to become parallel to the optical axis of the camera C, as shown in FIG. 13.

(First Embodiment of Pupil Detection)

Figure 10:
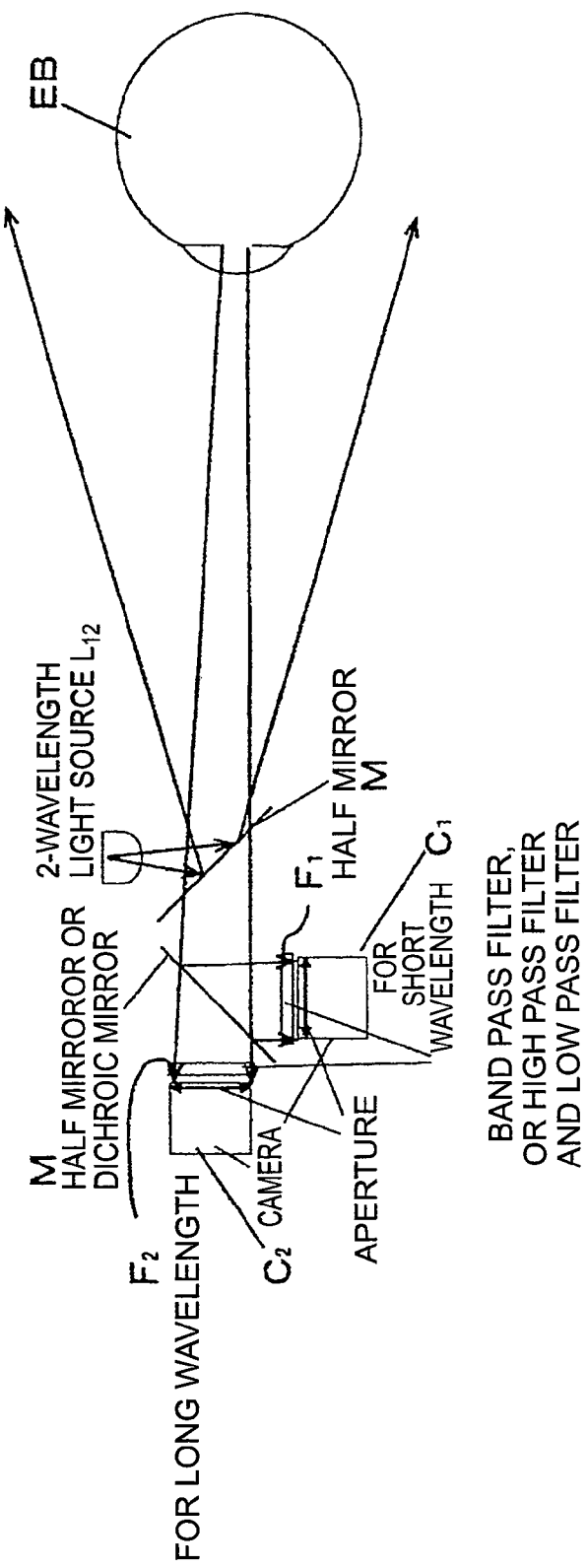
FIG. 10 is an optical path diagram illustrating a pupil detection device according to the present invention.

FIG. 10 is an optical path diagram illustrating a first exemplary disposition in a first embodiment of the pupil detection according to the present invention.

By means of a light source L12 including light emission sources having center wavelengths of 850 nm and 950 nm, an eyeball EB of the examinee is irradiated with near-infrared light of two wavelengths, via a half mirror M. The half mirror M and the light source L12 are disposed so that the optical axis of the above light source L12 substantially coincides with that of a camera C.

Here, as described earlier, it is possible to apply a combination of a short wavelength and a long wavelength respectively higher and lower relative to approximately 900 nm, and the wavelengths are not limited to the particular wavelengths described above.

The reflected light from the retina is made incident on the camera C through either the half mirror or a dichroic mirror M for wavelength separation at approximately 900 nm.

Here, when the half mirror M is used, there are disposed band pass filters F1, F2, each having as same center wavelength as each light source to each camera C1, C2. When the band pass filters are not used, a low pass filter F and a high pass filter F, each having a cutoff wavelength of approximately 900 nm, are disposed in front of the cameras. Additionally, two sets of light having different center wavelengths are separated as much as possible.

Figure 11:
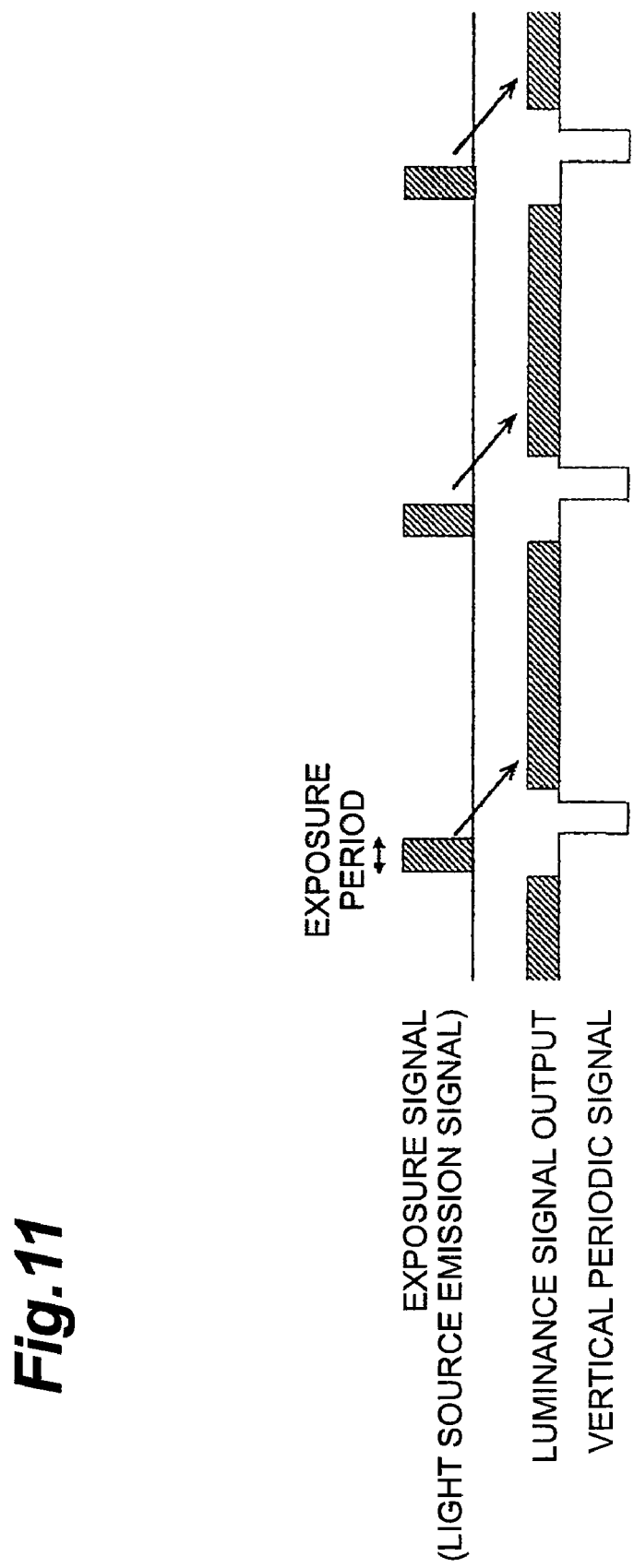
FIG. 11 is a time chart illustrating output timing of both an illumination light source and a camera.

The pupil is detected after calculating a difference between the images obtained by the two cameras C1, C2. At this time, to cut an external light (environment light) as much as possible, and also to reduce a blur in the pupil image, caused by the movement of the pupil produced as the head moves, to the possible extent, it is an effective method that the shutters of the two video cameras are opened for a short time (0.1 ms, for example) per frame, and a light source is lit only during that time, as shown in FIG. 11.

As one of the simplest implementation methods, a multi-channel image input board is inserted into a personal computer, and a progressive camera is employed as video camera.

Periodic external trigger signals generated by an oscillator or the like are input into the image input board. According to the above signals, exposure signals are output from the image input board to the cameras. The same signals are used as signals for lighting the two-wavelength light sources. By shortening the lighting time of the light sources, it is possible to extremely increase the current amount required during lighting, and make greater the ratio of a light amount by the light sources to a light amount by an external light, during the period when the shutters are open, and as a result, it is possible to drastically reduce the influence of the external light (environment light).

Figure 15:
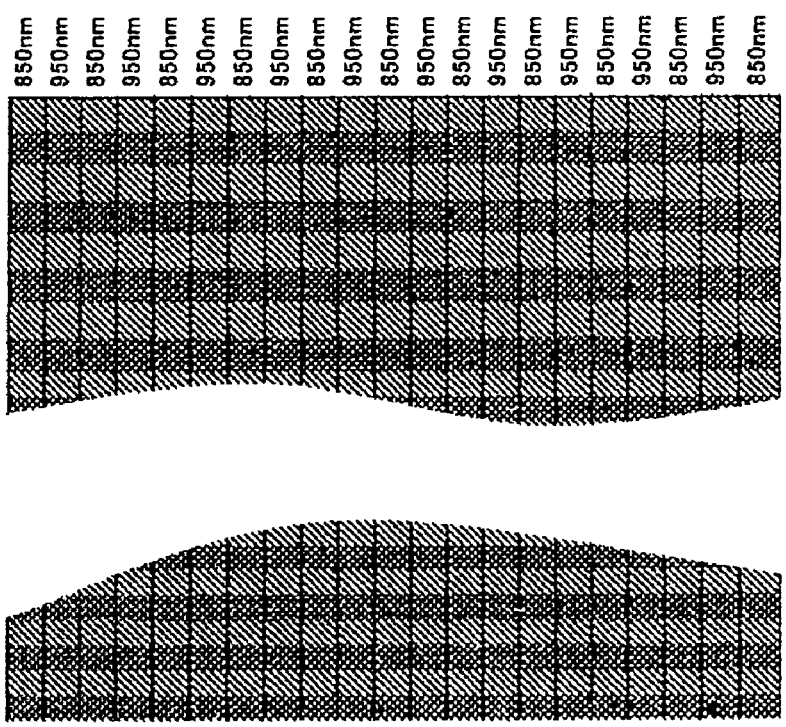
FIG. 15 is a diagram showing an image sensor of a camera.

FIG. 13 is an optical path diagram illustrating a second exemplary disposition in the first embodiment of the pupil detection according to the present invention. The above second exemplary disposition is configured of a single camera. In that case, as shown in FIG. 15, band pass filters having different center wavelengths in a stripe shape are disposed to cover an image sensor used in the camera, so as to be fit for pixels. Although filters of a vertical stripe are shown here, a horizontal stripe or a grid shape may be applicable. In any cases, the image difference is obtained between neighboring pixels covered with band pass filters having different center wavelengths, and a pupil is detected as a portion having a large luminance difference.

Additionally, in place of the band pass filters, it may also be possible to substitute a high pass filter and a low pass filter, each having a cutoff wavelength of approximately 900 nm. In that case, however, in order to reduce the influence of an environment light, it is desirable to mount on the camera aperture either a visible light cutoff filter or a wideband bandpass filter, which passes approximately 800 nm to approximately 1,000 nm.

FIG. 17 is an optical path diagram illustrating a third exemplary disposition of the first embodiment of the pupil detection according to the present invention. An objective lens 19, a lens 18, mirrors $M_1$, $M_2$ constitute an optical path forming means. A first camera is configured of a band pass filter $F_1$ having a center wavelength in the vicinity of a short wavelength (850 nm), a lens 13 and an image sensor $C_1$. A second camera is configured of a band pass filter $F_2$ having a center wavelength in the vicinity of a long wavelength (950 nm), a lens 14 and an image sensor $C_2$. The mirror $M_1$ is either a half mirror or a dichroic mirror, disposed on the optical axes of two cameras, thereby apparently enabling the optical axes of the two cameras to be substantially coincident. On the front face of the lens 19, an aperture common to the two cameras is formed. A half mirror $M_2$ for coupling illumination light sources is disposed on the examinee's side of the objective lens 19.

The light source 21 is constituted of a plurality of light-emitting elements 21a-21d, branching fibers 23a-23d, and a coupling unit 24. As to the above light-emitting elements 21a-21d, two are LEDs for long wavelength, and the remaining two are LEDs for short wavelength, and the respective LEDs are optically connected to the coupling unit 24 with the branching fibers 23a-23d. Here, as the light-emitting elements 21a-21d constituting the light source 21, generally a short-wavelength light source tends to have higher emission power, and therefore, it is also possible to allot one for short wavelength and the remaining three for long wavelength.

When four light-emitting elements 21a-21d emit, light having two wavelength components is synthesized by the coupling unit 24, and incident on the half mirror $M_2$. As a result, the light of two wavelength components is reflected toward the examinee's face in a state that the common optical axis in the camera aperture is kept substantially coincident with the optical axis of camera by the half mirror $M_2$. In other words, when viewed from the face side, the synthesized light is irradiated from inside the aperture including the common optical axis of camera. The face image including a bright pupil image produced by the above illumination and the face image including a dark pupil image are separated by the mirror $M_1$ after transmitting through the half mirror $M_2$, the lens 19, and the lens 18. Then, the light including the short wavelength light component transmits through the band pass filter $F_1$, and is imaged on the short-wavelength image sensor $C_1$ by means of the lens 13. On the other hand, the light including the long wavelength light component being reflected and separated by the mirror $M_1$ transmits through the band pass filter $F_2$, and is imaged on the long-wavelength image sensor $C_2$ by means of the lens 14.

Figure 12:
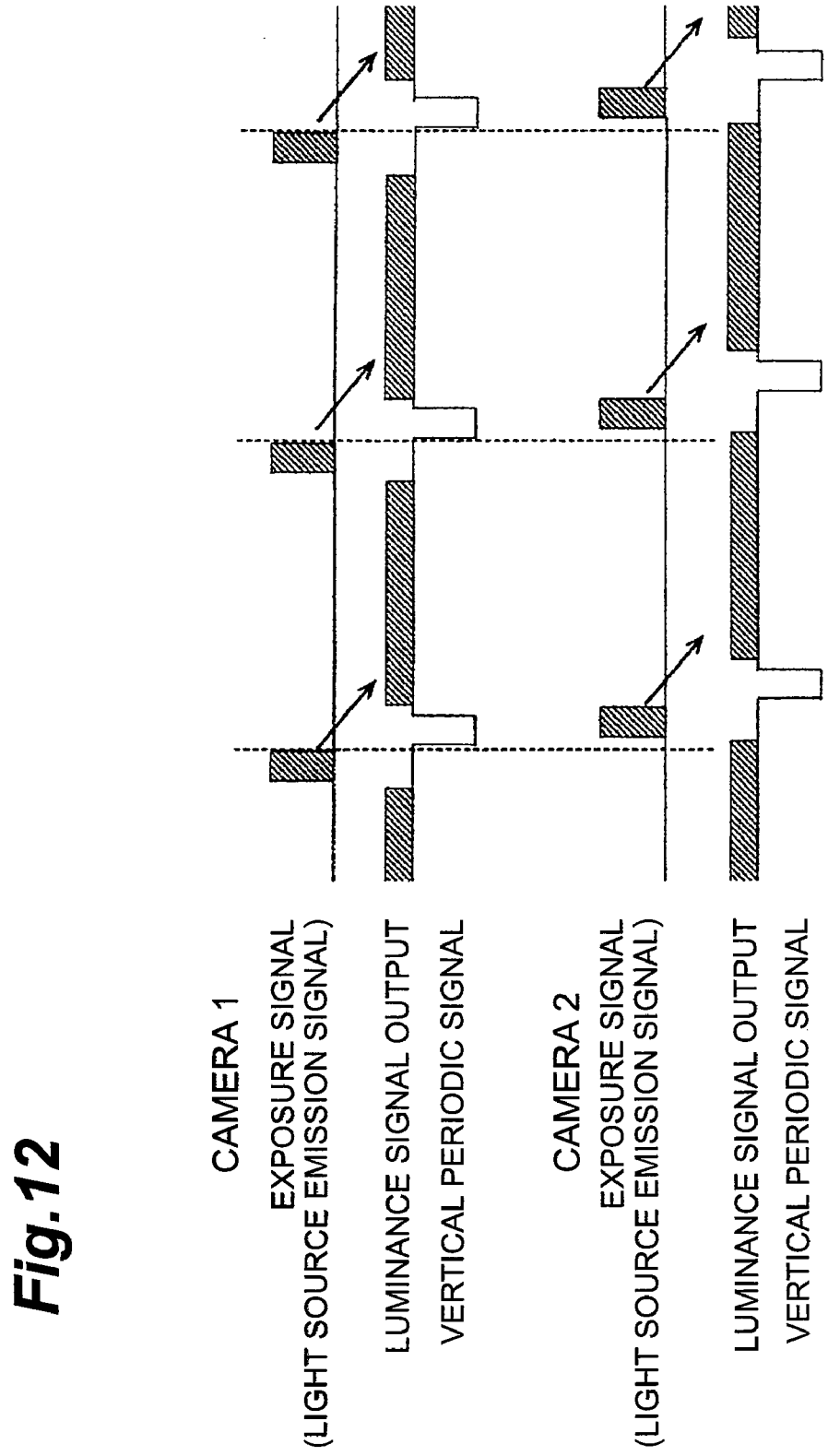
FIG. 12 is another time chart illustrating output timing of both an illumination light source and a camera.

Further, when the use of the band pass filter and the dichroic mirror is not desired due to some reason, as one of the simplest implementation method, it may be possible to consider a method such that two image input boards are inserted into one personal computer, so as to periodically input external trigger signals into the both boards, and by providing a delay in one image input board, thereby differentiating each exposure period of the two cameras, a deviation in the emission timing of the respective light sources of two wavelengths is produced, as shown in FIG. 12. If the exposure time is on the order of less than 1 ms, the exposure timing deviation between the cameras for image subtraction is 2 ms maximum, and accordingly, a blur caused by the movement of the pupil is substantially negligible, and the center of the pupil, etc. can be detected accurately. Needless to say, without provision of delay in the image input boards as described above, it is possible to input the external trigger signals, having initially mutual time differences, into the two image input boards, in a time-shifted manner. In addition, it may be possible to perform image subtraction at the time point when obtaining both of a pair of two images for subtraction, or at an earliest time just after one video signal obtained behind the other one is transferred to the personal computer. As such, in any cases, two images on which the image subtraction is to be performed are obtained in a time-shifted manner (asynchronously) at both exposing and video outputting.

(Second Embodiment of the Pupil Detection)

For the use in which a blur in the movement of the pupil is not worrying, it is not necessary to separate two wavelengths.

As shown in FIG. 13, an eye is irradiated with each light emission source of two-wavelength light sources in a two-wavelength LED (L12) via a half mirror M positioned in front of one camera, by alternately lighting on a frame-by-frame basis, or on a field-by-field basis in case of a NTSC (interlace scanning system) camera, and after subtracting temporally neighboring images obtained by the irradiation of each light emission source, a pupil image is detected through image processing.

Figure 14:
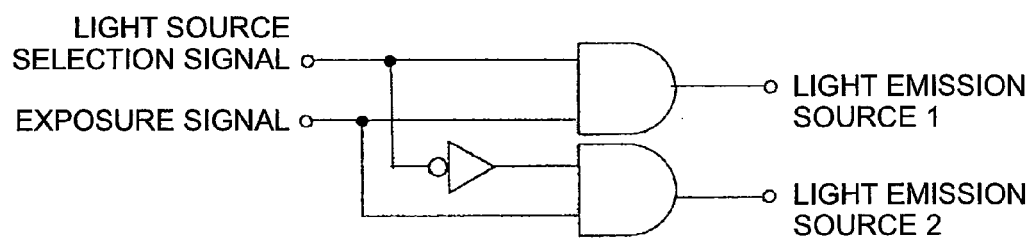
FIG. 14 is a circuit diagram illustrating a timing generation circuit of a light source selection signal and an exposure period.

As one of the simplest implementation methods, from an exposure signal shown in FIG. 11 and a signal output from an image input board for selecting a light emission source, it may be possible to newly generate an exposure signal for alternately lighting each light emission source, using a circuit shown in FIG. 14. In addition, the light emission source selection signal may be obtained by inputting signals such as a vertical synchronous video signal and the exposure signal from the image input board into a D flip-flop, and using the output thereof (in the D flip-flop output, a high level and a low level are alternately repeated at the rise timing or the fall timing of the input signal).

Additionally, in the above case also, in order to reduce the influence of environment light, desirably, either a visible light cutoff filter or a wideband band pass filter passing approximately 800 nm to approximately 1,000 nm is mounted on a camera aperture.

As such, the pupil detection device according to the present invention does not necessarily require two cameras. For example, in the exemplary disposition shown in FIG. 17, either a wideband band pass filter passing approximately 800 nm-approximately 1,000 nm or a band pass filter passing the vicinity of approximately 850 nm and the vicinity of approximately 950 nm at the front face of the lens 19 may be provided. Also, in place of the two image sensors $C_1$, $C_2$, an interlace scanning image sensor (camera) of the NTSC system, the PAL system, or the like, may be fixedly disposed at an intermediate position between the lens 18 and the lens 19, or alternatively, a non-interlace scanning image sensor (camera) may be fixedly disposed. In the case of the interlace scanning, a bright pupil image and a dark pupil image can be obtained separately by making a long-wavelength light source and a short-wavelength light source among the light sources 21a-21d alternately emit in synchronization with the occurrence timing of an odd-number field and an even-number field in the image signals of the image sensor, and further, a pupil is detected by performing subtraction between the obtained pixels of an odd-number line and the pixels of an even-number line neighboring the odd-number line. In the case of the non-interlace scanning, a bright pupil image and a dark pupil image can be obtained separately by making a long-wavelength light source and a short-wavelength light source among the light sources 21a-21d alternately emit in synchronization with the frames of the image sensor, and further, from the obtained pixels, a pupil is detected by performing subtraction between the corresponding pixels in the frames obtained at neighboring times. Additionally, in either case, in order to increase the accuracy in the pupil detection, preferably the shutter speed of the above image sensor is set to the order of 0.1 ms-1 ms, and the light emission sources 21a-21d are made to emit synchronously with the above shutter timing.

(Third Embodiment Performing Pupil Detection and Three-Dimensional Pupil Position Measurement)

To detect the eye of an examinee with high accuracy, three-dimensional position information of the pupil is important. Further, since it is possible to know from where the examinee is looking, the three-dimensional position of the pupil is an important information source in the field of human interface.

To measure the three-dimensional pupil position, stereo measurement is applied generally. Accordingly, there are required two systems, or more, of the optical system shown in FIGS. 10, 13, 17, etc. Specifically, a two-system pupil detection device having such the optical systems is disposed opposite to the examinee with a certain distance apart therefrom, and also at a certain distance apart from each other. Then, based on the two-dimensional position of the pupil detected by each pupil detection device, it is configured to enable measurement of the three-dimensional pupil position by means of stereo measurement.

In addition, originally, assuming that the LED with the light source itself being invisible is used, and when selecting a wavelength range of a camera having sensitivity tolerable for use, the wavelength range comes to a range of 850 nm-950 nm as center wavelength. In such the circumstance, a band pass filter having a considerably narrow bandwidth is required to optically separate more than two optical systems, in which two wavelengths are to be used in each optical system, and separation by means of the optical filter is considerably difficult. Therefore, it is appropriate to choose a time division method. Here, it may be possible to cause the light emission sources having two center wavelengths in each system to simultaneously emit, and apply wavelength separation.

In the above case, in the optical system using two cameras as shown in FIGS. 10 and 17, or in the optical system using one camera having the image sensor including mounted band pass filters of center wavelengths of 850 nm and 950 nm for neighboring pixels, it is sufficient if the emission by the light sources having two types of center wavelengths in the two-wavelength light sources may be performed simultaneously and in a slightly time-shifted manner for each system, and the shutter of each camera, having each light source mounted thereon, may be released synchronously with the above emission.

Industrial Applicability

According to the pupil detection device of the present invention, a pupil can be detected with accuracy. By the use thereof, it is possible to apply to the field of developing human interface in which a cursor movement on a personal computer screen is made correspondent to the moving amount of the pupil. Also, since the pupil detection can be performed even in an extremely different illumination environment, it is possible to apply to an industrial field of the development of driving support devices for detecting eyes, sleepiness and inattentive driving of a passenger car driver and a truck driver.

The invention claimed is:

1. A pupil detection device comprising: a camera; a light source; and a calculation system, for detecting a pupil by calculating an examinee's face image formed in the camera, the light source including:
a first illumination light source having a first wavelength light component which makes a bright pupil image by reflection in the examinee's pupil; and
a second illumination light source having a second wavelength light component which makes a dark pupil image by reflection in the examinee's pupil, and otherwise exhibiting the same illumination effect as that of the first illumination light source, the camera including:
a first image data acquisition system for obtaining first face image data using the first illumination light source; and
a second image data acquisition system for obtaining second face image data using the second illumination light source;

wherein the calculation system is operative for calculating the first image data and the second image data, so as to detect the pupil; and wherein the pupil detection device further includes an optical path forming system for irradiating light from an aperture of the camera by disposing the light source spaced off an optical axis of the camera, the optical path forming system including at least one reflector disposed for reflecting the light from the light source in a manner to have an optical axis thereof coincident with the optical axis of the camera, and for reflecting or transmitting the examinee's face image including the pupil generated by the light from the light source toward the camera.

2. The pupil detection device according to claim 1,
wherein the light source is configured such that optical axes of the independent first illumination light source and second illumination light source are synthesized by the optical path forming system so as to maintain a common optical axis, and the optical path is modified so that the common optical axis coincides with the optical axis of the camera.

3. The pupil detection device according to claim 1,
wherein the light source includes a first light emission source having a first wavelength light component, a second light emission source having a second wavelength light component disposed independently of the first light emission source, and a lens for disposing optical axes of the first and the second light emission sources mutually adjacent and parallel to each other, and is configured such that light of the first wavelength light component and light of the second wavelength light component are collectable with an identical directivity, and
wherein the optical path forming system includes a mirror disposed on the optical axis of the camera for modifying the optical path so that the optical axis of the light source coincides with that of the camera.

4. A pair of pupil detection devices according to claim 1, being disposed apart from the examinee by a certain distance and mutually apart from each other by a certain distance, and each detecting a pupil to measure a three-dimensional position of the pupil.

5. A pupil detection method for detecting a pupil by irradiating an examinee's face with light from a light source, forming a face image including an examinee's pupil in a camera, and then calculating the image formed in the camera using a calculation system, the pupil detection method comprising the steps of:
irradiating on the examinee's face, from an aperture of the camera, a first wavelength light component which makes a bright pupil image by reflection in the examinee's pupil, and a second wavelength light component which makes a dark pupil image by reflection in the examinee's pupil, the second wavelength light component otherwise exhibiting the same illumination effect as that of the first wavelength light component, from the light source, by disposing the light source spaced off an optical axis of the camera, and providing at least one reflector included in an optical path forming system and disposed for reflecting the light from the light source in such a manner that the optical axes of the first and second light components coincide with the optical axis of the camera;
by using the optical path forming system, reflecting or transmitting toward the camera the examinee's face image including the pupil, generated by the light from the light source;
by use of the camera, obtaining first image data using the first wavelength light component;
by use of the camera, obtaining second image data using the second wavelength light component; and
by the calculation system, calculating the first image data and the second image data, so as to detect the pupil.

6. The pupil detection device according to claim 2,
wherein the light source is independently disposed in such a manner that optical axes of the first illumination light source and the second illumination light source mutually intersect, and
wherein the optical path forming system is disposed in light emission directions of the first illumination light source and the second illumination light source, and includes a half mirror for synthesizing light by transmitting light from one of the first and the second illumination light sources and reflecting light from the other, and a mirror for modifying the optical path in such a manner that the optical axis of the synthesized light from the half mirror coincides with that of the camera.

* * * * *

UNITED STATES PATENT AND TRADEMARK OFFICE
CERTIFICATE OF CORRECTION

PATENT NO. : 8,358,337 B2　　　　　　　　　　　　　　　　　　　　　　　Page 1 of 1
APPLICATION NO. : 12/064481
DATED : January 22, 2013
INVENTOR(S) : Yoshinobu Ebisawa It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1171 days.

Signed and Sealed this
First Day of September, 2015

Michelle K. Lee
*Director of the United States Patent and Trademark Office*